United States Patent [19]

Plummer

[11] 4,130,657

[45] Dec. 19, 1978

[54] [1,1'-BIPHENYL]-3-YLMETHYL 3-(2,2-DIHALOETHENYL)-2,2-DIMETHYL-CYCLOPROPANECARBOXYLATES

[75] Inventor: Ernest L. Plummer, North Tonawanda, N.Y.

[73] Assignee: FMC Corporation, Philadelphia, Pa.

[21] Appl. No.: 844,099

[22] Filed: Oct. 20, 1977

[51] Int. Cl.$^2$ .................. C07C 69/74; A01N 9/30
[52] U.S. Cl. ................................. 424/305; 560/124
[58] Field of Search .................. 560/124; 424/305

[56] References Cited

U.S. PATENT DOCUMENTS 4,024,163  5/1977  Elliott ............................ 560/124

FOREIGN PATENT DOCUMENTS 1928540  1/1970  Fed. Rep. of Germany ........... 560/124

OTHER PUBLICATIONS

Chem. Abstr., 72:121192; (1970).
Elliott, "Synthetic Pyrethroids," American Chemical Society, Washington, D. C., 1977, pp. 1–28.
Elliott, Bull. Wld. Hlth. Org., 44, p. 315, (1970).
Sawada, et al., Bull. Chem. Soc., Japan, 45, p. 1206, (1972).

*Primary Examiner*—James O. Thomas, Jr.
*Assistant Examiner*—Michael Shippen
*Attorney, Agent, or Firm*—Richard L. Hansen; Henry R. Ertelt

[57] ABSTRACT

[1,1'-Biphenyl]-3-ylmethyl 3-(2,2-dihaloethenyl)-2,2-dimethylcyclopropanecarboxylates are disclosed and shown to control a broad spectrum of insects as well as acarids.

10 Claims, No Drawings

[1,1'-BIPHENYL]-3-YLMETHYL 3-(2,2-DIHALOETHENYL)-2,2-DIMETHYLCYCLOPROPANECARBOXYLATES

BACKGROUND OF THE INVENTION

1. Field of the Invention

This invention pertains to the field of bio-affecting compositions; more specifically, it pertains to novel carboxylic acid esters which are pyrethroid insecticides, to insecticidal and acaricidal compositions containing the novel esters, and to the use of the compositions for controlling insects and acarids.

2. Description of the Prior Art

Pyrethrins have long been of interest as insecticides. Ever since it was discovered that pyrethrins are organic esters, various synthetic modifications have been made in the carboxylic acid and in the alcohol moieties on either side of the ester linkage. Many of the synthetic pyrethroids are more effective than the natural pyrethrins, and recent modifications have overcome a chronic pyrethrin problem — instability to air and light.

The carboxylic acid moiety in the aforesaid esters is often a 2,2-dimethylcyclopropane-1-carboxylic acid with various substituents in the 3-position. A class of pyrethroids of current commercial interest contains the 2,2-dihaloethenyl group in the 3-position; for example, pyrethroids containing the 3-(2,2-dichloroethenyl)-and 3-(2,2-dibromoethenyl)-2,2-dimethylcyclopropanecarboxylic acid units are disclosed in Elliott, et al., U.S. Pat. No. 4,024,163.

Many variations in the alcohol moiety of the aforesaid esters have been disclosed also. The alcohols appearing in the most active pyrethroids of current commercial interest are well-known in the prior art and are described by the structural formula

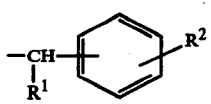

wherein $R^1$ is a hydrogen atom, an alkynyl group, a methyl, or a cyano group; and $R^2$ is a phenoxy group, a benzyl group, or a phenylthio group. Representative alcohols are 3-phenoxybenzyl alcohol and α-cyano-3-phenoxybenzyl alcohol.

According to M. Elliott, *Bull. Wld. Hlth. Org.*, 44, 315 (1970), it is "essential for powerful pyrethrin-like activity" that the alcohol moiety, represented by HO[C-D-E-F], contain certain structural units. It is necessary that the unit C be a tetrahedral carbon atom chemically bonded, not only to the alcoholic oxygen atom O, but to unit D, the remainder of a cyclopentenolone ring, a benzene or furan ring, or C≡C, so that "the carbon atoms in C, D, and E are coplanar." "The unit E is —CH₂—, —O—, or —CO—, or a sterically equivalent link, such that an unsaturated centre F (an olefinic or acetylenic bond, a conjugated system of double bonds, or an aromatic ring) can adopt a position skew to the direction defined by C, D, and E." The alcohol moieties in the most active of the pyrethroid esters of current commercial interest all contain a linking unit E, for example, —O— in the representative alcohols named above.

SUMMARY OF THE INVENTION

It has now been found, unexpectedly, that potent insecticides and acaricides result even though the linking unite E is absent from the pyrethroid structure. [1,1'-Biphenyl]-3-ylmethyl 3-(2,2-dihaloethenyl)-2,2-dimethylcyclopropanecarboxylates, wherein the halogen is chlorine or bromine, exhibit pronounced insecticidal and acaricidal activity. For example, the activity of [1,1'-biphenyl]-3-ylmethyl 3-(2,2-dichloroethenyl)-2,2-dimethylcyclopropanecarboxylate is comparable to the activity of 3-phenoxybenzyl 3-(2,2-dichloroethenyl)-2,2-dimethylcyclopropanecarboxylate against some species. Like the 3-phenoxybenzyl esters, the new pyrethroids are capable of both geometrical and optical isomerism, the biological activity varying somewhat according to the specific isomer.

As in the case of 3-phenoxybenzyl 3-(2,2-dichloroethenyl)-2,2-dimethylcyclopropanecarboxylate, the pure cis geometrical isomer of [1,1'-biphenyl]-3-ylmethyl cis, trans-3-(2,2-dichloroethenyl)-2,2-dimethylcyclopropanecarboxylate is a more active insecticide and acaricide than the pure trans isomer, and the activity of [1,1'-biphenyl]-3-ylmethyl 3-(2,2-dichloroethenyl)-2,2-dimethylcyclopropanecarboxylate is a function of the cis/trans ratio.

Although the preparation and testing of the racemic ester is described specifically below, the pure optical isomers also display biological activity in varying degrees. The terms, [1,1'-biphenyl]-3-ylmethyl 3-(2,2-dichloroethenyl)-2,2-dimethylcyclopropanecarboxylate and [1,1'-biphenyl]-3-ylmethyl 3-(2,2-dibromoethenyl)-2,2-dimethylcyclopropanecarboxylate, are intended to include generically all optical and geometrical isomers of the named compounds and mixtures thereof.

The positionally isomeric [1,1'-biphenyl]-2-ylmethyl 3-(2,2-dichloroethenyl)-2,2-dimethylcyclopropanecarboxylate, although exhibiting insecticidal activity, is less active.

Also within the contemplation of this invention are insecticidal and acaricidal compositions comprising a biologically effective amount of [1,1'-biphenyl]-3-ylmethyl-3-(2,2-dihaloethenyl)-2,2-dimethylcyclopropanecarboxylate in admixture with an agriculturally acceptable carrier and a method of controlling insects and acarids which comprises applying to the locus where control is desired an insecticidally effective amount of [1,1'-biphenyl]-3-ylmethyl 3-(2,2-dichlorovinyl)-2,2-dimethylcyclopropanecarboxylate.

DETAILED DESCRIPTION OF THE INVENTION

Preparation of [1,1'-biphenyl]-3-ylmethyl 3-(2,2-dichloroethenyl)-2,2-dimethylcyclopropanecarboxylate and the dibromo analog are illustrated in the following examples. Unless otherwise indicated, all temperatures are in degrees centigrade and pressures are in millimeters of mercury. Proton chemical shifts, taken from nmr spectra, are reported with respect to tetramethylsilane in ppm.

EXAMPLE 1

Preparation of [1,1'-Biphenyl]-3-ylmethyl 3-(2,2-Dichloroethenyl)-2,2-dimethylcyclopropanecarboxylate A. Using [1,1'-Biphenyl]-3-ylmethanol A mixture of [1,1'-biphenyl]-3-ylmethanol (4.6 g, 0.025 mole), prepared by the method of G. S. Hammond and C. E. Reeder, *J. Am. Chem. Soc.*, 80, 573 (1958), pyridine (2.0 g, 0.025 mole), and 50 ml of methylene chloride was cooled to 0° under a dry nitrogen atmosphere, and 3-(2,2-dichloroethenyl)-2,2-dimethylcyclopropanecarbonyl chloride (5.68 g, 0.025 mole), which may be prepared according to the method of Farkas, et al., *Coll. Czech. Chem. Comm.*, 24, 2230 (1959), dissolved in 5 ml of methylene chloride, was added dropwise to the stirred mixture over a period of 15 minutes. The mixture was then stirred for about 16 hours at room temperature and then contacted with 50 g of ice in a separatory funnel. The ice was allowed to melt, and the aqueous and organic phases were separated. The aqueous phase was extracted twice with 50 ml portions of chloroform, and the extracts were combined with the organic phase. The combined organic phase was twice washed with 50 ml portions of cold 2N hydrochloric acid, then once with 100 ml of a saturated solution of sodium chloride, then twice with 50 ml portions of cold 2N sodium hydroxide, and, finally, twice with 200 ml portions of a saturated solution of sodium chloride. After drying the organic phase over anhydrous magnesium sulfate, the solvent was removed on a rotary evaporator, leaving an oily residue weighing 9.1 g. The residue was distilled in a short-path, air-bath heated Kugelrohr distillation apparatus at a pressure of 0.25 mm; after removing residual low boilers from the residue, the product, [1,1'-biphenyl]-3-ylmethyl cis,trans-3-(2,2-dichloroethenyl)-2,2-dimethylcyclopropanecarboxylate (7.74 g, 82.3% yield), distilled at a temperature above 130° C. and was collected as a straw-colored oil. The oil was 41/59 cis/trans based on the nmr spectrum, the ratio being the same as that in the starting cyclopropanecarbonyl chloride.

Analysis: Calculated for $C_{21}H_{20}Cl_2O_2$: C,67.21; H,5.37; Found: C,67.39; H,5.66. nmr ($CDCl_3$): 1.17(s, 3H); 1.22(s, 3H); 1.26(s, 3H); 1.30(s, 3H); 1.62–2.41(m, 4H); 5.19(s, 2H); 5.23(s, 2H); 5.63(d, 1H); 6.34(dd, 1H); 7.20–7.77(m, 18H).

The pure cis and trans isomers were separated from the cis,trans mixture by high pressure liquid/solid chromatography on a silica column using a mixture of ethyl acetate and n-hexane (1:75) as the eluting liquid. The identities of the two isomers were established by reference to their nmr spectra, especially the patterns at 5.62 ppm and 6.31 ppm for the trans and cis isomers, respectively, which are believed to represent the 1-protons of the 3-(2,2-dichloroethenyl) groups differentially deshielded by the 1-carboxylate group.

For the cis isomer: nmr ($CDCl_3$): 1.23(s, 3H); 1.26(s, 3H); 1.80–2.20(m, 2H); 5.19(s, 2H); 6.31(dd, 1H); 7.18–7.76(m, 9H). For the trans isomer: nmr ($CDCl_3$): 1.20(s, 3H); 1.33(s, 3H); 1.60–2.42(m, 2H); 5.22(s, 2H); 5.62(d, 1H); 7.20–7.73(m, 9H).

B. From 3-Bromomethylbiphenyl

Potassium hydroxide (2.0 g, 0.032 mole) was dissolved in 7 ml of water. To this solution was added 3-(2,2-dichloroethenyl)-2,2-dimethylcyclopropanecarboxylic acid (6.6 g, 0.032 mole), which may be prepared according to the method of Farkas, et al., loc. cit. After dissolution, 100 ml of heptane was added, and the mixture was heated under reflux using a DeanStarke trap to remove the water from the mixture. The dry mixture was then cooled to 60°, and a solution of 3-bromomethylbiphenyl (7.5 g, 0.032 mole) and 0.1 g of 1,4-diazabicyclo[2.2.2]octane in 60 ml of acetonitrile was added. 3-Bromomethylbiphenyl may be prepared according to the method of M. Gomberg and J. C. Pernert, *J. Am. Chem. Soc.*, 48, 1372 (1926) and H. O. Huisman, et al., *Rec. Trav. Chim.*, 71, 899 (1951). The mixture was then heated under reflux for 5.5 hours. After cooling to room temperature, the reaction mixture was contacted with 100 g of ice in a separatory funnel, and when the ice had melted the phases were separated. The aqueous phase was saturated with sodium chloride before being extracted twice with 100 ml portions of heptane. The heptane extracts and the organic phase were combined, and the combined organic phase was washed with one 200 ml portion of a saturated sodium chloride solution. The solvent was removed from the organic phase using a rotary evaporator, leaving an oily, straw-colored residue weighing 9.9 g. The oil was distilled in a short path, air-bath heated Kugelrohr distillation apparatus at a pressure of 0.25 mm. After removing low boilers from the oil at a temperature below 145°, [1,1'-biphenyl]-3-ylmethyl 3-(2,2-dichloroethenyl)-2,2-dimethylcyclopropanecarboxylate (6.5 g, 54.4% yield) was obtained at a temperature of 165°–175°.

EXAMPLE 2

Preparation of [1,1'-Biphenyl]-3-ylmethyl 3-(2,2-Dibromoethenyl)-2,2-dimethylcyclopropanecarboxylate A. From 3-Bromomethylbiphenyl

[1,1'-Biphenyl]-3-ylmethyl 3-(2,2-dibromoethenyl)-2,2-dimethycyclopropanecarboxylate was prepared by the method described in Example 1B above using potassium hydroxide (0.66 g, 0.12 mole), 3-(2,2-dibromoethenyl)-2,2-dimethylcyclopropanecarboxylic acid (5.3 g, 0.12 mole), which may be prepared according to the method of Elliott, et al., U.S. Pat. No. 4,024,163, 3-bromomethylbiphenyl (2.7 g, 0.12 mole), and 0.1 g of 1,4-diazabicyclo[2.2.2]octane.

The [1,1'-biphenyl]-3-ylmethyl cis,trans-3-(2,2-dibromoethenyl)-2,2-dimethylcyclopropoanecarboxylate, obtained by distillation, was purified by liquid/solid chromatography. The oily trans isomer was then distilled at 168°/0.25 mm in a short-path, air-bath heated Kugelrohr distillation apparatus. The distilled [1,1'-biphenyl]-3-ylmethyl trans-3-(2,2-dibromoethenyl)-2,2-dimethylcyclopropanecarboxylate had the following physical characteristics.

Analysis: Calculated for $C_{21}H_{20}Br_2O_2$: C,54.33; H,4.34; Found: C,55.22; H,4.47. nmr ($CDCl_3$): 1.12(s, 3H); 1.24(s, 3H); 1.77–2.29(m, 2H); 5.15(s, 2H); 6.10(d, 1H); 7.05–7.65(m, 9H).

In the normal use of the insecticidal and acaricidal esters of the present invention, the esters usually will not be employed free from admixture or dilution, but ordinarily will be used in a suitable formulated composition compatible with the method of application and comprising a biologically effective amount of [1,1'-biphenyl]-3-ylmethyl 3-(2,2-dihaloethenyl)-2,2-dimethylcyclopropanecarboxylate. The esters of this invention, like most pesticidal agents, may be blended with the agriculturally acceptable surface-active agents and carriers normally employed for facilitating the dispersion of active ingredients, recognizing the accepted fact that the formulation and mode of application of an insecticide or acaricide may affect the activity of the material. The present esters may be applied, for example, as sprays, dusts, or granules to the area where pest control is desired, the type of application varying of course with the pest and the environment. Thus, the esters of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the esters. The granule particles are relatively large, a diameter of about 400-2500 microns typically. The particles are either impregnated with the ester from solution or coated with the ester, adhesive sometimes being employed. Granules generally contain 1-15%, preferably 3-10%, active ingredient as the biologically effective amount.

Dusts are admixtures of the esters with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects and acarids contains 10 parts of [1,1'-biphenyl]-3-ylmethyl 3-(2,2-dichloroethenyl)-2,2-dimethylcyclopropanecarboxylate, 30 parts of bentonite clay, and 60 parts of talc.

The esters of the present invention may be made into liquid concentrates by dissolution or emulsification in suitable liquids and into solid concentrates by admixture with talc, clays, and other known solid carriers used in the pesticide art. The concentrates are compositions containing, as a biologically effective amount, about 5-50% [1,1'-biphenyl]-3-ylmethyl 3-(2,2-dihaloethenyl)-2,2-dimethylcyclopropanecarboxylate, such as [1,1'-biphenyl]-3-ylmethyl cis,trans-3-(2,2-dichloroethenyl)-2,2-dimethylcyclopropanecarboxylate, and 95-50% inert material, which includes surface-active dispersing, emulsifying, and wetting agents. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects and acarids contains 1.5 parts each of sodium lignosulfonate and sodium laurylsulfate as wetting agents, 25 parts of [1,1'-biphenyl]-3-ylmethyl cis,-trans-3-(2,2-dichloroethenyl)-2,2-dimethylcyclopropanecarboxylate, and 72 parts of bentonite clay.

Useful liquid concentrates include the emulsifiable concentrates, which are homogeneous liquid or paste compositions readily dispersed in water or other liquid carriers. They may consist entirely of the ester with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally coprises about 1-15% by weight of the insecticidal and acaricidal composition.

Other useful formulations include simple solutions of the active ingredient in a solvent in which it is completely soluble at the desired concentration, such as acetone or other organic solvents.

A biologically effective amount of [1,1'-biphenyl]-3-ylmethyl 3-(2,2-dihaloethenyl)-2,2-dimethylcyclopropanecarboxylate in an insecticidal and acaricidal composition diluted for application is normally in the range of about 0.001% to about 2% by weight. Many variations of spraying and dusting compositions known in the art may be used by substituting the esters of this invention into compositions known or apparent to the art.

The insecticidal and acaricidal compositions of this invention may be formulated with other active ingredients, including other insecticides, nematicides, acaricides, fungicides, plant growth regulators, fertilizers, etc. In using the compositions to control insects and acarids, it is only necessary that an insecticidally effective amount of [1,1'-biphenyl]-3-ylmethyl 3-(2,2-dihaloethenyl)-2,2-dimethylcyclopropanecarboxylate be applied to the locus where control is desired. For most applications, an insecticidally effect amount of [1,1'-biphenyl]-3-ylmethyl 3-(2,2-dihaloethenyl)-2,2-dimethylcyclopropanecarboxylate will be about 75 to 4000 g per hectare, preferably 150 g to 3000 g per hectare.

The insecticidal and acaricidal activity of [1,1'-biphenyl]-3-ylmethyl cis,trans-3-(2,2-dichloroethenyl)-2,2-dimethylcyclopropanecarboxylate containing 41/59 cis/trans was evaluated as follows:

The ester (0.25 g) was dissolved in 20 ml of acetone, and this solution was dispersed in 180 ml of water containing one drop of isoctyl phenyl polyethoxyethanol. Aliquots of this solution, containing 1250 ppm ester, were diluted with appropriate amounts of water to provide test solutions containing lesser amounts of the active ingredient.

Test organisms and techniques were as follows:

Activities against the Mexican bean beetle (*Epilachna varivestis* Muls.) and the southern armyworm (*Spodoptera eridania* [Cram.]) were evaluated by dipping the leaves of pinto bean plants into the test solution and, when the foliage had dried, infesting the leaves with the appropriate immature insects; activity against the pea aphid (*Acyrthosiphon pisum* [Harris]) was evaluated on broad bean plants whose leaves were dipped before infestation with adult aphids; activity against twospotted spider mites (*Tetranychus urticae* Koch) was evaluated on pinto bean plants whose leaves were dipped after infestation with adult mites; activities against the milkweed bug (*Oncopeltus fasciatus* [Dallas]) and the plum curculio (*Conotrachelus nenuphar* [Herbst]) were evaluated by spraying the test solutions into glass dishes or jars containing the adult insects. All organisms in the tests were maintained in a holding room at 80° F. and 50% relative humidity for an exposure period of 48 hours. At the end of this time, the dead and living insects or mites were counted, and the percent kill was calculated. Results of these tests are summarized in Tables I-III.

The residual contact activity of the esters was also determined on the same organisms using the techniques described above, except that in each case the treated surface was allowed to dry and was exposed to normal light and air for 7 days before introduction of the mites or insects. The results of these tests also appear in Tables I and II as the figures in parenthesis.

[1,1'-Biphenyl]-3-ylmethyl 3-(2,2-dichloroethenyl)-2,2-dimethylcyclopropanecarboxylate is highly effective, both upon initial application and after exposure to light and air. [1,1'-Biphenyl]-3-ylmethyl 3-(2,2-dibromoethenyl)-2,2-dimethylcyclopropanecarboxylate also exhibits pesticidal activity.

TABLE I

ACTIVITY OF [1,1'-BIPHENYL]-3-YLMETHYL CIS,TRANS-3-(2,2-DICHLORETHENYL)-2,2-DIMETHYLCYCLOPROPANECARBOXYLATE[c]

Percent Kill[a]

| Conc. ppm. | Mexican Bean Beetle | Southern Armyworm | Pea Aphid | Twospotted Spider Mite | Milkweed Bug | Plum Curculio |
|---|---|---|---|---|---|---|
| 1250 | (100) | (100) | 100 (100) | 100[b] | 100 (100) | 100 (100) |
| 312 | 100 (49)[b] | 100 (100) | 100 (58)[b] | 48 | 100 (100)[b] | 95[b] (98)[b] |
| 156 | | 100 | 100 | | 100 | 80 |
| 78 | 100 (15)[b] | 100[b] (84)[b] | 88[b] (40)[b] | 14 | 94[b] (85)[b] | 27[b] (11)[b] |
| 39 | 81[b] | 100 | 73[b] | | 52[b] | 6 |
| 20 | 63[b] (0) | 99[b] (17) | 29[b] (0) | | 26[b] (15) | (0) |
| 10 | 42[b] | 100[b] | 11 | | | |
| 5 | 22[b] | 63 (0) | | | | |
| 2.5 | | 30 | | | | |
| 1.2 | | 6 (0) | | | | |
| 0.6 | | 0 | | | | |

[a]The figures in parenthesis refer to residual contact activity 7 days after treatment.
[b]Average of two or more tests
[c]41/59 cis/trans

TABLE II

ACTIVITY OF [1,1'-BIPHENYL]-3-YLMETHYL CIS-3-(2,2-DICHLOROETHENYL)-2,2-DIMETHYLCYCLOPROPANECARBOXYLATE

Percent Kill[a]

| Conc. ppm. | Mexican Bean Beetle | Southern Armyworm | Pea Aphid | Twospotted Spider Mite | Milkweed Bug | Plum Curculio |
|---|---|---|---|---|---|---|
| 1250 | | | | 100 | | |
| 312 | (25) | (100) | (100) | 99 | (90) | 100 (100) |
| 156 | | 100 | 100 | | 100 | |
| 78 | (0) | 100 (100) | 90 (40) | 57 | 83 (63) | 23 (40) |
| 39 | 82 | 100 | 90 | | 20 | |
| 20 | 41 | 100 (18) | 2 75 | | 10 | |
| 10 | 41 | 100 | | | | |
| 5 | 13 | | | | | |

[a]The figures in parenthesis refer to residual contact activity 7 days after treatment.

TABLE III

ACTIVITY OF [1,1'-BIPHENYL]-3-YLMETHYL TRANS-3-(2,2-DICHLOROETHENYL)-2,2-DIMETHYLCYCLOPROPANECARBOXYLATE

Percent Kill

| Conc. ppm. | Mexican Bean Beetle | Southern Armyworm | Pea Aphid | Twospotted Spider Mite | Milkweed Bug |
|---|---|---|---|---|---|
| 1250 | | 100 | 100 | 0 | 100 |
| 312 | 100 | 100 | 100 | | 100 |
| 78 | 100 | 100 | 100 | | 65 |
| 20 | 89 | | | | |

I claim:

1. A [1,1'-Biphenyl]-3-ylmethyl 3-(2,2-dihaloethyenyl)-2,2-dimethylcyclopropanecarboxylate wherein the halogen is chlorine or bromine.

2. [1,1'-Biphenyl]-3-ylmethyl 3-(2,2-dibromoethenyl)-2,2-dimethylcyclopropanecarboxylate.

3. [1,1'-Biphenyl]-3-ylmethyl 3-(2,2-dichloroethenyl)-2,2-dimethylcyclopropanecarboxylate.

4. The compound of claim 3 which is the cis geometrical isomer.

5. The compound of claim 3 which is the trans geometrical isomer.

6. An insecticidal or acaracidal composition comprising a insecticidally or acaricidally effective amount of a compound of claim 1 in admixture with an agriculturally acceptable carrier.

7. A composition of claim 6 which contains a surface active agent.

8. A method of controlling insects or acarids which comprises applying to the locus where control is desired an insecticidally or acaricidally effective amount of a compound of claim 1.

9. A method of claim 8 wherein the compound of claim 1 is [1,1'-biphenyl]-3-ylmethyl 3-(2,2-dichloroethenyl)-2,2-dimethylcyclopropanecarboxylate.

10. The method of claim 9 wherein the [1,1'-biphenyl]-3-ylmethyl 3-(2,2-dichloroethenyl)-2,2-dimethylcyclopropaencarboxylate is the cis geometrical isomer.